United States Patent
Ogawa

(10) Patent No.: US 8,642,493 B2
(45) Date of Patent: Feb. 4, 2014

(54) PROCESS FOR PRODUCING LOWER-HYDROCARBON AROMATIZATION CATALYST AND LOWER-HYDROCARBON AROMATIZATION CATALYST

(75) Inventor: Yuji Ogawa, Kawagoe (JP)

(73) Assignee: Meidensha Corporation, Tokyo (JP)

( * ) Notice: Subject to any disclaimer, the term of this patent is extended or adjusted under 35 U.S.C. 154(b) by 270 days.

(21) Appl. No.: 13/063,340

(22) PCT Filed: Sep. 29, 2009

(86) PCT No.: PCT/JP2009/066889
§ 371 (c)(1),
(2), (4) Date: Mar. 10, 2011

(87) PCT Pub. No.: WO2010/061683
PCT Pub. Date: Jun. 3, 2010

(65) Prior Publication Data
US 2011/0172089 A1    Jul. 14, 2011

(30) Foreign Application Priority Data
Nov. 25, 2008    (JP) .................................. 2008-298909

(51) Int. Cl.
*B01J 29/06*    (2006.01)
(52) U.S. Cl.
USPC ................... 502/62; 502/60; 502/63; 502/64; 502/71; 502/85
(58) Field of Classification Search
USPC ................. 502/60, 63, 64, 71, 77, 79, 85, 62
See application file for complete search history.

(56) References Cited

U.S. PATENT DOCUMENTS

| | | | |
|---|---|---|---|
| 5,541,146 A * | 7/1996 | Chang et al. | 502/64 |
| 5,552,357 A * | 9/1996 | Lago et al. | 502/63 |

(Continued)

FOREIGN PATENT DOCUMENTS

| | | |
|---|---|---|
| CN | 85 1 04995 A | 1/1987 |
| CN | 1214961 A | 4/1999 |
| GB | 2 160 517 A | 12/1985 |
| JP | 61-14117 A | 1/1986 |

(Continued)

OTHER PUBLICATIONS

F. Solymosi et al., Aromatization of Methane over Supported and Unsupported Mo-Based Catalysts, Journal of Catalysis 165, Article No. CA971478, 1997, pp. 150-161.

*Primary Examiner* — Elizabeth Wood
(74) *Attorney, Agent, or Firm* — Foley & Lardner LLP

(57) ABSTRACT

[Task] To improve activity of a lower hydrocarbon aromatization catalyst and the catalyst stability.
[Solving Means] In a method for producing a lower hydrocarbon aromatization catalyst to produce an aromatic compound by a catalytic reaction using a lower hydrocarbon as a raw material, the catalyst includes a metallosilicate on which molybdenum is supported, a silane in 0.75 weight % or more relative to the metallosilicate component is supported, and the catalyst is prepared by conducting a compressive shaping without adding an inorganic binder that binds particles of the catalyst. As a result, the lower hydrocarbon aromatization catalyst maintains a sufficient shape-retaining property even by a compressive shaping in a binderless manner. Stability of the catalyst and activity of the catalyst improve by subjecting the lower hydrocarbon aromatization catalyst to a compressive shaping in a binderless manner. Its advantageous effect is conspicuous when the amount of addition in terms of silicon oxide is 0.75 weight %.

2 Claims, 1 Drawing Sheet

(56) References Cited

U.S. PATENT DOCUMENTS

| | | | |
|---|---|---|---|
| 6,777,583 B2* | 8/2004 | Beck et al. | 585/475 |
| 8,278,237 B2* | 10/2012 | Yamada et al. | 502/77 |
| 2003/0055305 A1* | 3/2003 | Beck et al. | 585/643 |
| 2003/0113248 A1* | 6/2003 | Mohr et al. | 423/213.2 |
| 2005/0020435 A1* | 1/2005 | Beck et al. | 502/63 |
| 2006/0052235 A1* | 3/2006 | Bai et al. | 502/66 |

FOREIGN PATENT DOCUMENTS

| | | |
|---|---|---|
| JP | 07-258658 A | 10/1995 |
| JP | 3755955 B2 | 1/2006 |
| JP | 3835765 B2 | 8/2006 |
| JP | 2006-305408 A | 11/2006 |
| JP | 3745885 B2 | 12/2006 |
| JP | 2007-014894 A | 1/2007 |

\* cited by examiner

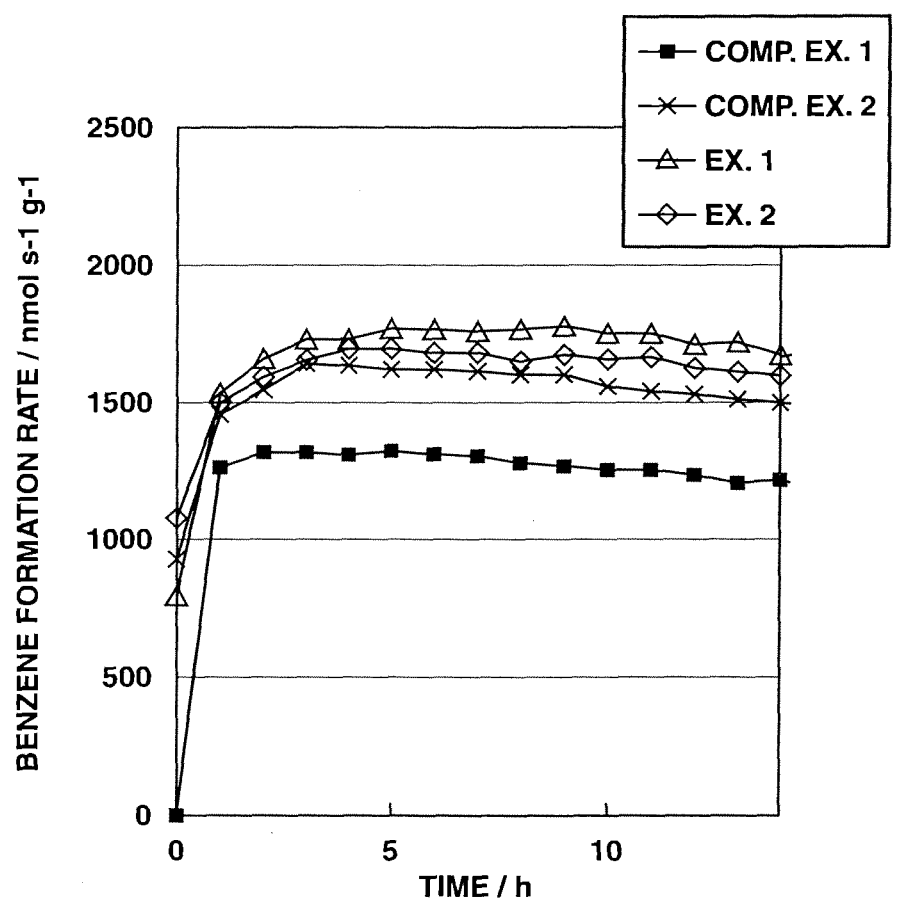

PROCESS FOR PRODUCING LOWER-HYDROCARBON AROMATIZATION CATALYST AND LOWER-HYDROCARBON AROMATIZATION CATALYST

TECHNICAL FIELD

The present invention relates to a high-degree use of natural gas, biogas and methane hydrate, in which methane is a main component. Natural gas, biogas, and methane hydrate are regarded as the most effective energy resources as global warming measures, and an interest in its use technique is increasing. Methane resource making use of its clean property attracts an attention as the next generation new organic resource and as a hydrogen resource for fuel cells.

In particular, the present invention relates to a catalytic chemical conversion technique for effectively producing aromatic compounds, in which benzene and naphthalenes, which are raw materials of chemical products such as plastics, are main components, and a high-purity hydrogen gas, from methane.

BACKGROUND TECHNIQUE

As a process for producing aromatic compounds, such as benzene, and hydrogen from a lower hydrocarbon, particularly methane, one is known in which methane is reacted in the presence of a catalyst. As the catalyst upon this, molybdenum supported on a ZSM-5 series zeolite is said to be effective (Non-patent Publication 1).

However, even in the case of using these catalysts, it has problems that carbon is precipitated in a large amount and that conversion of methane is low.

In order to solve this problem, there has been proposed a catalyst in which a catalyst material such as Mo (molybdenum) is supported on a porous metallosilicate, as disclosed, for example, in Patent Publication 1 or Patent Publication 2. It has been confirmed in Patent Publication 1 and Patent Publication 2 that lower hydrocarbons are efficiently turned into aromatic compounds by using a catalyst in which a metal component is supported on a porous metallosilicate as a support having a micropore diameter of 7 angstroms, and along with this a high purity hydrogen is obtained.

Then, in Patent Publication 3 and Patent Publication 4, zeolite is chemically modified with a silane compound, prior to supporting a metal component, such as molybdenum, on zeolite, in order to improve selectivity and yield of the catalytic reaction.

That is, benzene selectivity has improved, and, since catalyst deterioration by coking is reduced, catalyst stability has improved remarkably, by conducting a molecular-level surface treatment, such as silane treatment, on zeolite (metallosilicate).

PRIOR ART PUBLICATIONS

Patent Publications

Patent Publication 1: Japanese Patent Publication No. 3755955
Patent Publication 2: Japanese Patent Publication No. 3745885
Patent Publication 3: Japanese Patent Publication No. 3835765
Patent Publication 4: Japanese Patent Application Publication No. 2007-014894

Non-Patent Publications

Non-patent Publication 1: JOURNAL OF CATALYSIS, 1997, vol. 165, p. 150-161.

SUMMARY OF THE INVENTION

Task to be Solved by the Invention

In the above-mentioned conventional techniques, in the case of practical catalyst, it is necessary to shape the form of catalyst into pellet-like, spherical, ring-like or honeycomb-like, or the like in order to bring a lower hydrocarbon gas, such as methane, and the catalyst into contact efficiently in the reaction container.

However, zeolite crystals have a high specific surface area of crystals, and have a weak binding strength of crystals with each other, resulting from surface charge characteristics as solid acid.

Therefore, it is necessary to shape it by adding an inorganic binder such as clay. By the influence of this inorganic binder, there has been a problem of lowering of catalyst characteristics by the occurrence of side reactions that have no relation with the uses, the occurrence of coking, or the like.

Furthermore, the optimum amount of addition of the silane treatment in the silane treatment written in Patent Publication 3 is 0.25 weight %. On the other hand, the most desirable amount of addition of the silane treatment in the silane treatment written in Patent Publication 4 is 0.5 weight %. This amount of addition of the silane treatment, however, cannot shape the catalyst particles in a binderless manner.

It is an object of the present invention to make it possible to shape the catalyst without using inorganic binder and to provide a method for producing a lower hydrocarbon aromatization catalyst to improve catalyst activity and its stability.

Means for Solving the Task

A method for producing a lower hydrocarbon aromatization catalyst of the present invention to achieve the above object is characterized in that a lower hydrocarbon is used as a raw material, and that, in a method for shaping a lower hydrocarbon aromatization catalyst to produce aromatic compounds by catalytic reactions, the catalyst comprises a molybdenum-supported metallosilicate, a silane in 0.75 weight % or greater relative to the metallosilicate component is supported, and the catalyst is prepared by a compressive shaping without adding an inorganic binder that binds particles of the catalyst.

Furthermore, a lower hydrocarbon aromatization catalyst of the present invention to achieve the above object is characterized in that a lower hydrocarbon is used as a raw material, and that, in a lower hydrocarbon aromatization catalyst to produce aromatic compounds by catalytic reactions, the catalyst comprises a molybdenum-supported metallosilicate, a silane in 0.75 weight % or greater relative to the metallosilicate component is supported, and the catalyst is prepared by a compressive shaping without adding an inorganic binder that binds particles of the catalyst.

According to a method for producing a lower hydrocarbon aromatization catalyst of the present invention, since adhesion of metallosilicate (zeolite particles) improves, it is possible to provide a lower hydrocarbon aromatization catalyst, which makes a shaping possible without using an inorganic binder.

Advantageous Effect of the Invention

According to the above invention, it is possible to produce a lower hydrocarbon aromatization catalyst in a binderless manner, and activity of the catalyst and the catalyst stability improve.

BRIEF DESCRIPTION OF THE DRAWINGS

[FIG. 1] A change of benzene formation rate over time in the case of a reaction of each catalyst of Comparative Examples 1 and 2 and Examples 1 and 2 with a methane gas (containing 6% $H_2$ and 0.5% $CO_2$).

MODE FOR CONDUCTING THE INVENTION

According to a method for producing a lower hydrocarbon aromatization catalyst according to an embodiment of the present invention, the lower hydrocarbon aromatization catalyst is shaped without using an inorganic binder such as clay binder, thereby improving characteristics of the catalyst.

That is, it is a method for shaping a lower hydrocarbon aromatization catalyst, in which adhesion among zeolite crystals is increased by supporting on the surface of zeolite crystals a silane in an amount that is greater than that of silane necessary for the zeolite surface treatment, in which a sufficient shape-retaining property is maintained only by a pressing treatment of a compressive pressing, and in which the catalyst activity characteristics are improved.

In the following, examples of a lower hydrocarbon aromatization catalyst according to the present invention are explained in detail. However, zeolite used as a catalyst, a silane compound used in the surface treatment, and a catalyst precursor supported on zeolite are not limited to those of the present examples, and it suffices to use zeolite, a silane compound, and a precursor such as molybdenum, which are exemplified by the descriptions of Patent Publications 3 and 4.

In the present invention, as a metallosilicate on which a catalyst metal is supported, for example, in the case of aluminosilicate, it is possible to mention molecular sieve 5A, faujasite (NaY and NaX), ZSM-5 and MCM-22, which are porous bodies formed of silica and alumina. Furthermore, it can be exemplified by zeolite supports characterized by being porous bodies containing phosphoric acid as a main component and having micropores and channels of 6-13 angstroms, such as ALPO-5, VPI-5, etc., and meso-microporous supports, such as FSM-16, MCM-41, etc., containing silica as a main component and partially containing alumina as a component and characterized by cylindrical micropores (channels) of meso-micropores (10-1000 angstroms). Furthermore, besides the above aluminosilicates, it is possible to use a metallosilicate formed of silica and titania, etc. as the catalyst.

Furthermore, a metallosilicate used in the present invention is desirably one having a surface area of 200-1000 $m^2/g$ and micro- and meso-micropores in a range of 5-100 angstroms. Furthermore, in case that the metallosilicate is an aluminosilicate, it is possible to use one of silica/alumina=1-8000, which is similar to the content ratio of silica to alumina (silica/alumina) of porous bodies that are generally available. It is, however, more preferable to make silica/alumina within a range of 10-100 in order to conduct the aromatization reaction of lower hydrocarbons of the present invention with a practical conversion of lower hydrocarbons and selectivity to aromatic compounds.

Furthermore, in the present invention, the lower hydrocarbons signify methane and saturated and unsaturated hydrocarbons having a carbon number of 2-6. These saturated and unsaturated hydrocarbons having a carbon number of 2-6 can be exemplified by ethane, ethylene, propane, propylene, n-butane, isobutane, n-butene and isobutene, etc.

EXAMPLES

1. Production of a Lower Hydrocarbon Aromatization Catalyst (in the Following it is Abbreviated as Catalyst)

Comparative Example 1

Catalyst Shaped by Using an Inorganic Binder (the Amount Added in Terms of Silicon Oxide: 0.75 Weight %)

(1) Surface Treatment

As the silane compound, aminopropyltriethoxysilane (APTES) was selected. APTES was dissolved in ethanol, and HZSM-5 was impregnated therewith.

Then, a dry powder was obtained by a spray-dry treatment, followed by a baking at 550° C. for 6 hours, thereby obtaining SiHZSM-5 supporting silane in 0.75 weight % in terms of silicon oxide, relative to the untreated HZSM-5.

(2) Supporting of Molybdenum

An impregnation aqueous solution prepared by ammonium molybdate $((NH_4)_6Mo_7O_{24})$ is stirred, and SiHZSM-5 subjected to the above-mentioned (1) surface treatment is impregnated with the impregnation aqueous solution under this stirred condition. Then, it was dried and baked at 550° C. for 8 hours, thereby obtaining Mo/SiHZSM-5 supporting molybdenum in 6 weight % relative to the weight of the zeolite after the silane treatment.

(3) Shaping
(3-a) Mixing

Mixing of inorganic components: Mo/SiHZSM-5 (82.5 weight %), clay (12.5 weight %), and glass fibers (5 weight %)

Total mixing: the inorganic components (76.5 weight %), organic binder (17.3 weight %), and water (24.3 weight %)
(3-b) Shaping Method The inorganic component, the organic binder, and the water were mixed together by the mixing proportion, followed by blending and kneading by a kneading means (kneader). Then, this mixture was shaped into a rod shape (diameter 2.4 mm×length 5 mm) by a vacuum extruder. The extrusion pressure upon this shaping was set at 2-8 MPa.

In general, a catalyst support used for reforming hydrocarbons is used as a flow bed catalyst by using particles having a particle diameter of several micrometers to several hundreds micrometers. In the method for producing the catalyst support in this case, the catalyst support material, the organic binder, the inorganic binder (normally clay is used) and water are mixed together into a slurry, followed by granulation shaping (no shaping pressure) with a spray drier and then baking. In this case, since there is no shaping pressure, the amount of clay added to be added as a baking assistant in order to secure the baking rate was about 40-60 weight %. Here, the catalyst shaping is conducted by a high-pressure shaping using a vacuum extruder. With this, it is possible to reduce the amount of an additive, such as clay, added as a baking assistant to 15-25 weight %. Therefore, it is possible to improve the catalyst activity, too.

(3-c) Drying and Baking

In the drying step, it was dried at 70° C. for about 12 hours and then dried at 90° C. for 36 hours in order to remove water added in the shaping step. In the baking step, it was baked in the air at 550° C. for 8 hours. The baking temperature in the baking step was made to be a range of 550-800° C. This is because lowering of strength of the support occurs at lower than 550° C., and because lowering of characteristics (activity) occurs at higher than 800° C. The temperature increase rate and the temperature decrease rate in the baking step were set at 90-100° C./hr. Upon this, in order to prevent the organic binder added upon the shaping from burning instantaneously, the organic binder was removed by keeping the temperature two times within a temperature range of 250-500° C. for about 2 to 6 hours. This is because the organic binder burns instantaneously to cause lowering of strength of the baked body, in case that the temperature increase rate and the temperature decrease rate are greater than the above rate and that the time for removing the organic binder is not taken.

Comparative Example 2

Catalyst Shaped by Using an Inorganic Binder (the Amount Added in Terms of Silicon Oxide: 1.1 Weight %)

The catalyst production method of Comparative Example 2 is the same as the mixing and production method of Comparative Example 1 except that in the silane treatment the amount of silane added to HZSM-5 is different.

In Comparative Example 2, Mo/SiHZSM-5 was obtained by supporting silane in 1.1 weight % in terms of silicon oxide relative to the untreated HZSM-5. Molybdenum was supported in 6 weight % relative to the weight of the zeolite after the silane treatment.

Comparative Example 3

Catalyst Shaped in a Binderless Manner (the Amount Added in Terms of Silicon Oxide: 0.5 Weight %).

(1) Surface Treatment

As the silane compound, aminopropyltriethoxysilane (APTES) was selected. APTES was dissolved in ethanol, and HZSM-5 was impregnated therewith.

Then, a dry powder was obtained by a spray-dry treatment, followed by a baking at 550° C. for 6 hours, thereby obtaining SiHZSM-5 supporting silane in 0.5 weight % in terms of silicon oxide, relative to the untreated HZSM-5.

(2) Impregnation of Molybdenum

An impregnation aqueous solution prepared by ammonium molybdate $((NH_4)_6Mo_7O_{24})$ is stirred, and SiHZSM-5 subjected to the above-mentioned (1) surface treatment is impregnated with the impregnation aqueous solution under this stirred condition. Then, it was dried and baked at 550° C. for 8 hours, thereby obtaining Mo/SiHZSM-5 supporting molybdenum in 6 weight % relative to the weight of the zeolite after the silane treatment.

(3) Pressure Shaping

Methanol in 10 weight % relative to the powder after the catalyst preparation was added and was caused to blend therein. Then, the powder was put into a powder compacting shaping mold of φ24 mm and a depth of 30 mm and then compacted with a pressure of 2.5 metric ton/cm². A disk-like object compacted was broken with a hammer, followed by granulation to have a particle diameter of 2 mm. Then, the granulated object was dried by a drier to evaporate ethanol, thereby obtaining a binderless granular catalyst.

Example 1

Catalyst Shaped in a Binderless Manner (the Amount Added in Terms of Silicon Oxide: 0.75 Weight %)

The catalyst production method of Example 1 is the same as the mixing and production method of Comparative Example 3 except that in the silane treatment the amount of silane added to HZSM-5 is different.

In Example 1, Mo/SiHZSM-5 was obtained by supporting silane in 0.75 weight % in terms of silicon oxide relative to the untreated HZSM-5. Furthermore, molybdenum was supported in 6 weight % relative to the weight of the zeolite after the silane treatment.

Example 2

Catalyst Shaped in a Binderless Manner (the Amount Added in Terms of Silicon Oxide: 1.1 Weight %)

The catalyst production method of Example 2 is the same as the mixing and production method of Comparative Example 3 except that in the silane treatment the amount of silane added to HZSM-5 is different.

In Example 2, Mo/SiHZSM-5 was obtained by supporting silane in 1.1 weight % in terms of silicon oxide relative to the untreated HZSM-5. Furthermore, molybdenum was supported in 6 weight % relative to the weight of the zeolite after the silane treatment.

2. Evaluation of the Catalysts of Comparative Examples and Examples (1) Vibration Experiment The binderless granular catalyst (Example 1, Example 2 and Comparative Example 3) was put into a cylinder of φ30 mm and a depth of 10 cm, and then vibrated by a vibrator.

In the catalysts of Example 1 and Example 2, only the particles in about 2% of the total amount were collapsed. On the other hand, in the catalyst of Comparative Example 3, the particles of more than 80% of the total amount were collapsed.

From the above results, in the case of using it as a binderless catalyst, in the surface treatment by silane compound, it is necessary that the amount of the addition in terms of silicon oxide is 0.75 weight % or more.

(2) Evaluation of the Catalyst Performance

Next, benzene was formed (MTB reaction) by conducing a contact reaction of a raw material gas (containing hydrogen in 6% and carbon dioxide in 0.5% besides methane) containing as a main component methane as a lower hydrocarbon with the catalysts of Comparative Examples 1 and 2 and Examples 1 and 2, and their stabilities and catalyst activities were examined. Here, a comparison was made by examining the change over time of the benzene formation rate. The experimental conditions are shown in the following.

<Experimental Conditions>
Temperature: 1023K
Pressure: 0.3 MPa
Raw material gas: $CH_4$ (containing 6% $H_2$ and 0.5% $CO_2$) flow rate 3000 ml-h$^{-1}$-g$^{-1}$
Catalyst charge amount: pellet catalyst 14 g (the catalyst except inorganic binder was in 11.5 g), binderless catalyst 11.55 g In the analysis, hydrogen, argon and methane were analyzed by TCD gas chromatography, and aromatic hydrocarbons such as benzene, toluene, xylene, naphthalene, and the like were analyzed by FID gas chromatography.

FIG. 1 shows changes over time of benzene formation rate ($nmol \cdot s^{-1} \cdot g^{-1}$) in the case that HZSM-5 type zeolites (Comparative Examples 1 and 2 and Examples 1 and 2) subjected to silane treatment were used for aromatizing a lower hydrocarbon.

As is clear from FIG. 1, it is understood that the benzene formation rate improves by shaping the catalyst in a binderless manner, as compared with a pellet catalyst shaped by using an inorganic binder, even if the catalyst production method other than the shaping method is the same. This advantageous effect can be confirmed in both catalysts added in amounts of 0.75 weight % and 1.1 weight % in terms of silicon oxide. In particular, the advantageous effect is conspicuous in the catalyst added in an amount of 0.75 weight % in term of silicon oxide.

Furthermore, the formation rate lowers little by little with the passage of time in the catalysts (Comparative Examples 1 and 2) shaped by using an inorganic binder. On the other hand, as is clear from FIG. 1, benzene is stably formed without lowering of the formation rate in the catalysts (Examples 1 and 2) shaped in a binderless manner, as compared with the catalysts shaped by using an inorganic binder.

That is, the catalyst stability is also improved by shaping the catalyst in a binderless manner. Therefore, as compared with conventional techniques (Cited References 3 and 4), the catalyst according to the present invention maintains a stable catalytic activity, although the reaction is conducted under a condition (weight, time and rate of methane gas) that the catalytic activity lowering such as coking tends to occur.

As explained above, according to a method for producing a lower hydrocarbon aromatization catalyst according to the present invention, adhesion among the catalyst particles each other increases, and it is possible to shape the lower hydrocarbon aromatization catalyst in a binderless manner. Therefore, activity of the lower hydrocarbon aromatization catalyst and the catalyst stability improve.

Furthermore, it is needless to say that various modifications are possible to the present invention explained based on the above examples in the scope of the invention described in the Scope of Claims and that these also belong to the technical scope of the present invention.

The invention claimed is:

1. In a method for shaping a lower hydrocarbon aromatization catalyst to produce an aromatic compound by a catalytic reaction using a lower hydrocarbon as a raw material,
   a method for producing the lower hydrocarbon aromatization catalyst, characterized in that the catalyst comprises a H/ZSM-5 on which molybdenum is supported,
   that aminopropyltriethoxysilane in an amount of from 0.75 weight % to 1.1 weight % relative to the H/ZSM-5 is supported, and
   that the catalyst is prepared by conducting a compressive shaping without adding an inorganic binder that binds particles of the catalyst.

2. In a lower hydrocarbon aromatization catalyst to produce an aromatic compound by a catalytic reaction using a lower hydrocarbon as a raw material,
   the lower hydrocarbon aromatization catalyst being characterized in that the catalyst comprises a H/ZSM-5 on which molybdenum is supported,
   that aminopropyltriethoxysilane in an amount of from 0.75 weight % to 1.1 weight % relative to the H/ZSM-5 is supported, and
   that the catalyst is prepared by conducting a compressive shaping without adding an inorganic binder that binds particles of the catalyst.

* * * * *